(12) United States Patent
Wright

(10) Patent No.: US 9,204,811 B2
(45) Date of Patent: Dec. 8, 2015

(54) PHYSICAL ACTIVITY MONITORING SYSTEMS

(75) Inventor: David Wright, Nottingham (GB)

(73) Assignee: Myzone Limited, Isle of Man (GB)

( * ) Notice: Subject to any disclaimer, the term of this patent is extended or adjusted under 35 U.S.C. 154(b) by 0 days.

(21) Appl. No.: 14/126,120

(22) PCT Filed: Jun. 16, 2011

(86) PCT No.: PCT/GB2011/000906
§ 371 (c)(1),
(2), (4) Date: Mar. 10, 2014

(87) PCT Pub. No.: WO2012/172273
PCT Pub. Date: Dec. 20, 2012

(65) Prior Publication Data

US 2015/0025401 A1    Jan. 22, 2015

(51) Int. Cl.
*A61B 5/024* (2006.01)
*A61B 5/00* (2006.01)

(52) U.S. Cl.
CPC ........... *A61B 5/02438* (2013.01); *A61B 5/0002* (2013.01); *A61B 5/0015* (2013.01); *A61B 5/6823* (2013.01)

(58) Field of Classification Search
CPC .. A61B 5/024; A61B 5/02438; A61B 5/0002; A61B 5/0015; A61B 5/6823; Y10S 482/00
USPC .......................................... 600/382, 509, 519
See application file for complete search history.

(56) References Cited

U.S. PATENT DOCUMENTS

| 6,259,944 B1 * | 7/2001 | Margulis .............. A61B 5/0002 128/903 |
| 6,416,471 B1 | 7/2002 | Kumar et al. |
| 2001/0044588 A1 | 11/2001 | Mault |
| 2002/0082867 A1 | 6/2002 | MacCarter et al. |
| 2003/0167079 A1 * | 9/2003 | Birnbaum et al. .............. 607/60 |
| 2005/0250458 A1 * | 11/2005 | Graham et al. ............... 455/121 |
| 2008/0109051 A1 | 5/2008 | Splinter |
| 2008/0309481 A1 | 12/2008 | Tanaka |
| 2011/0093210 A1 | 4/2011 | Matsuzaki |

FOREIGN PATENT DOCUMENTS

| GB | 2420628 | 5/2006 |
| WO | 99/30613 A1 | 6/1999 |

* cited by examiner

*Primary Examiner* — Christopher D Koharski
*Assistant Examiner* — Michael Carey
(74) *Attorney, Agent, or Firm* — Steptoe & Johnson LLP

(57) ABSTRACT

A system for monitoring physical activity, in which activity data for an individual is be captured and stored whether the activity takes place in a health club or away from the health club (e.g. outdoors). The proposed approach is to capture heart rate data using an individual heart rate monitor (e.g. a chest belt) that has inbuilt memory for storing the heart rate data. The data is uploaded from the belt to a database, preferably a database that is accessible over the Internet, via a receiver station that will typically be located in a health club where the user is a member.

25 Claims, 3 Drawing Sheets

PHYSICAL ACTIVITY MONITORING SYSTEMS

CROSS-REFERENCE TO RELATED APPLICATIONS

This application claims priority to International Application No. PCT/GB2011/000906, filed Jun. 16, 2011, which is incorporated by reference in its entirety.

FIELD OF THE INVENTION

The present invention relates to systems for monitoring physical activity of individuals by measuring their heart rate.

BACKGROUND OF THE INVENTION

In recent years, the importance of physical fitness has gained popular recognition as part of a healthy life style. Regular exercise is encouraged by society generally as well as government initiatives, including initiatives in schools. There is also a growing realisation amongst employers that a physically fit work force can be an important contributor to bottom line profits, with many companies providing schemes to encourage exercise, including subsidised or free health club membership for example. Physical fitness tends to lead to increased energy, reduced stress, improved efficiency when working and helps maintain health (e.g. reducing the risks of heart disease).

Monitoring physical activity is an important part of any fitness regime. Heart rate monitoring is one form of monitoring that is regularly used. It can be used as a measure of the intensity of physical activity, expressed for example as a percentage of an individual's maximum heart rate ('HRmax'), and can be used to calculate calories burned during exercise. Maximum heart rate is a well known parameter in the health and fitness industry and there are various well known formula for calculating it. In some cases an individual may monitor their heart rate during exercise to help them maintain a particular effort level relative to their own capabilities.

Heart rate monitors are available in various forms. One common form includes a chest strap transmitter and a wrist worn receiver. The chest strap component uses EKG techniques to detect the heart rate and transmits a signal to the wrist receiver, typically via an analogue radio signal or more recently an ANT+ signal, that displays the measured heart rate in real time to the user. In some health club-based systems, a user's heart rate data might be transmitted to an exercise device that they are using to be displayed to the user on a screen of the exercise device.

Also known are heart rate monitors where the heart rate data is stored temporarily in the wrist receiver, from where it can be uploaded to the user's personal computer in order that they can keep a personal record of their physical activity.

SUMMARY OF THE INVENTION

A general aim of the present invention is to provide systems and methods for monitoring physical activity, in which activity data for an individual can be captured, stored and shared (e.g. with health club, employer, school or doctor's surgery), whether the activity takes place in a health club or away from the health club (e.g. outdoors). The proposed approach is to capture heart rate data using an individual heart rate monitor (e.g. a chest belt) that has inbuilt memory for storing the heart rate data. The data is uploaded from the belt to a database, preferably a database that is accessible over the Internet, via a receiver station that will typically be located in a health club where the user is a member (receivers may be located elsewhere, e.g. in schools, doctor's surgeries and corporate offices). The user's data can then be accessed from the database by the user and anyone else who is authorised to access it, such as employees (e.g. trainers) at their health club, their employer, their doctor or their school.

Accordingly, in a first aspect, the invention provides a system for monitoring physical activity, the system comprising:

a plurality of heart rate monitors that can be assigned to individuals, each heart rate monitor comprising a detector for creating heart rate data that provides a measure of the individual's heart rate, a memory for storing the heart rate data, and a transmitter for transmitting the heart rate data;

at least one receiver station comprising a receiver for receiving heart rate data transmitted from the plurality of heart rate monitors;

a data management server connected by a communications network to the receiver station, to receive the heart rate data from the receiver station over the network; and a database associated with the data management server for storing the heart rate data received by the data management server.

The heart rate monitors may be chest belts, worn by the users of the system. They may detect the user's heart rate in a known manner, for example using EKG technology.

The memory for the heart rate monitor may be any of a number of suitable types. Preferably it is non-volatile memory, for example flash memory, that can retain the data without consuming power. The memory is preferably erasable in order that the stored heart rate data can be erased once it has been uploaded to the receiver station. The memory is preferably integrated with the heart rate monitor (e.g. chest belt).

The memory is preferably sized to be able to store at least one month's heart rate data for a typical user, for example 15 hours or 131,000 heart beats. The data may be time stamped to associate each data item or groups of data items with a specific date and time. The data preferably also includes a unique identifier for the heart rate monitor and/or the user of the monitor, so that when the data is stored in the database it can be associated with the relevant user account.

The transmitter for the heart rate monitor may be any of a number of suitable types. For example, it may be an analogue radio transmitter (e.g. 5.4 khz), an ANT+ transmitter, a 'blue tooth' transmitter or a 'blue tooth LE' transmitter. The heart rate monitor may comprise multiple transmitters of different types. Preferably the range of the transmitter (that is the maximum distance between the transmitter and the receiving station for reliable transmission of the data) is at least 50 meters.

Preferably the heart rate monitor is configured to automatically (i.e. without user intervention) transfer the heart rate data to the receiving station. When the heart rate monitor is in range of the receiving station, it may continuously transmit data to the receiving station. Alternatively, it may transmit data periodically, at predetermined time intervals. In another alternative, the data may be transmitted at the end of an exercise session. The end of an exercise session may be determined, for example, by a pre-determined period of inactivity, e.g. 15 seconds. "Inactivity" may be defined by the user's heart beat returning to a resting heart beat (e.g. a predefined user specific value or an arbitrary value set in the system)

and/or no heart beat being detected (because the user has removed or otherwise disabled the heart rate monitor.

In addition to or as an alternative to automatic upload of the heart beat data, the upload may be initiated by the command of a user (either the individual wearing the heart rate monitor or another). The command may, for example, be through operation of a control on the heart rate monitor or may be a command entered at a receiver station or hub of the system for instance.

The heart rate data is preferably deleted from the memory of the heart rate monitor once it has been successfully transmitted to the receiver station. The receiver station may send a signal back to the heart rate monitor to confirm a successful transfer of data.

Where the heart rate monitor is not in range of a receiver station, the data is stored in the memory of the heart rate monitor until a receiver station is within range and then the upload of data commences. In order that a heart rate monitor can determine whether a receiver station is in range, the or each receiver station may periodically transmit at polling signal that the heart rate monitor can detect. The range may be, for example, within 100 meters for upload of continuous data, or within 20 meters for upload of stored data. Alternatively, the heart rate monitor can periodically transmit a polling signal that will be detected and responded to by any receiving station that is within range. In the case of receiver station receiving both stored data and continuous data, the receiver station may have a separate antenna for receiving stored data and a separate antenna for receiving continuous data. In some embodiments, stored data will be uploaded from the heart rate monitor to the receiver at a rate of 2 hours of stored data per second.

The transmitter is preferably integrated with the heart rate monitor (e.g. chest belt). Especially in the case where the memory is also integrated with the monitor, so that the detector, memory and transmitter are all contained within one package, the means the heart rate monitor can be a single, self-contained unit. For instance, the heart rate monitor can be a self-contained chest belt that can be used without the necessity for a wrist unit (although a wrist unit may optionally be used, for example to provide a real-time display of heart rate).

The heart rate monitor may be battery powered. The battery or batteries may be replaceable by the user. Alternatively, the battery or batteries may be rechargeable and fixed within the monitor.

The heart rate monitor may switch itself into a 'standby' (low or no power consumption) mode after a predetermined period of inactivity, e.g. 5 minutes.

In some embodiments the heart rate monitor, e.g. chest belt, will be sweat and water resistance. In other embodiments the heart rate monitor may be waterproof.

The receiver station can be shared by multiple users. In some embodiments it is a dedicated unit installed in a fixed location, where it can be shared by multiple users of the system. Typical locations include health clubs, workplaces, doctor's surgeries and schools. The receiver station is preferably capable of receiving heart beat data from at least 100 heart beat monitors.

Multiple receiver stations may be installed in a given location (e.g. health club) to provide wider coverage and/or to cater for the expected number of users. Where multiple receiver stations are used, data from each of the receiver stations may be sent to the data management server, over the network, via a shared hub to which each of the receiver stations is attached by a communications link. The communications link for each receiver station may be a wired or a wireless link. One or more receiver stations may be integrated with the hub. The hub may take the form of a fixed installation, which may be powered by Mains power.

Alternatively, the hub may have its own integrated power source (e.g. a battery power source) so that is can be portable. In other embodiments the hub can be a conventional PC with appropriate software installed to provide the desired hub functionality.

The hub or, especially in the case of an installation with only a single receiver station, a receiver station may incorporate a management console for managing aspects of the system. For example, the console may include a facility for adding new users to the system and modifying or adding data associated with users. The console may be a conventional personal computer with installed software to provide the console functions. In some embodiments the console is a virtual machine (e.g. a virtual PC) hosted remotely from the location of the hub or receiver station that is accessed via a PC or a thin client terminal installed at the hub or receiver station.

The data management server preferably also provides access to the stored heart rate data and/or data derived from the heart rate data. Access to the data may be provided, for example, through personal computers (e.g. desktop PCs, laptops, tablets), smart phones, or other data processing devices that can connect to the data management server over the communications network.

Typically, an individual user's data will be associated in the database with an account for that user. Access by the user themselves and others to a particular user account, and the data associated with it, can be controlled using conventional protocols for managing access to data. For example, users of the system can be forced to provide authentication credentials (e.g. a user name and a password) before being allowed access to data associated with one or more user accounts.

In some embodiments the system may further comprise a studio console that incorporates or is linked to (e.g. wirelessly) a receiver station. The studio console is configured to receive heart rate data from the plurality of heart rate monitors and to provide a display output that can drive one or more screens to display the heart rate data, or data derived from it, for one or more users. For example, the screen may simultaneously display percentage effort level (i.e. heart rate as a percentage of the individual's recommended maximum heart rate) for a plurality of users, e.g. the users participating in a group exercise class, calculated from the heart rate data received at the studio console. Maximum heart rate (HRmax) for each user will typically be pre-entered in the system, having being calculated using a known formula or selected with the assistance of a fitness or health care professional for example.

The communications network via which the receiver stations are connected to the data management server (optionally via a hub) may be a private or a public network. In preferred embodiments, the communications network is the Internet. In other embodiments, the network can be a corporate network.

In some embodiments, the receiver station may receive data from other devices, for example, blood pressure monitors, weight scales and body fat analyzers. The data from these devices may be sent to the data management server, in a similar way as the heart rate data.

In a second aspect, the invention provides a heart rate monitor for use with the system of the first aspect, the heart rate monitor comprising a detector for creating heart rate data that provides a measure of an individual's heart rate, a memory for storing the heart rate data, and a transmitter for transmitting the heart rate data to a receiver station, wherein the detector, memory and transmitter are incorporated in a single package.

The features of the heart rate monitor set forth above in the discussion of the system of the first aspect are equally applicable to this second aspect.

In a third aspect, the invention provides a receiver station for use with the system of the first aspect, the receiver station comprising a receiver for receiving heart rate data transmitted from the plurality of heart rate monitors.

The features of the receiver station set forth above in the discussion of the system of the first aspect are equally applicable to this third aspect.

In a fourth aspect, the invention provides a data management server for the system of the first aspect, the server being connectable by a communications network to a receiver station, to receive the heart rate data from the receiver station over the network and having an associated database for storing heart rate data received by the data management server.

The features of the data management server set forth above in the discussion of the system of the first aspect are equally applicable to this fourth aspect.

In a fifth aspect, the invention provides a hub for the system of the first aspect, the hub comprising means for connecting (e.g. wirelessly) to a plurality of receiver stations via a communications link, the hub further comprising an integral receiver station.

The features of the hub set forth above in the discussion of the system of the first aspect are equally applicable to this fifth aspect.

In a sixth aspect the invention provides a method of collecting physical activity data from a plurality of individuals, each individual having been provided with a heart rate monitor capable of recording and storing heart rate data and transmitting the heart rate data to a receiving station, the method comprising:
  receiving at a receiving station heart rate data for the plurality of individuals from their respective heart rate monitors when the monitors are in range to transmit data to the receiving station; and
  sending received heart rate data from the receiving station to a data management server over a communications network.

The step of sending heart rate data to the data management server may comprise sending the data from the receiving station to a hub, which may be shared by a plurality of receiving stations, and sending the data from the hub to the data management server over the communications network.

In preferred embodiments, the receiving station is located in a health club. Where a hub is used, the hub may be in the same location (e.g. health club) as the receiving station.

In another aspect the invention provides a computer program, comprising computer program code that when executed on a computer or a computer network can cause the computer or computer network to function as one or more of:
  the receiver station of the system of the first aspect;
  the hub of the system of the first aspect; and
  the data management server of the system of the first aspect.

In a further aspect, the invention provides a computer program, comprising computer program code that when executed on a computer or a computer network can cause the computer or computer network to operate in accordance with the method of the sixth aspect.

BRIEF DESCRIPTION OF THE DRAWINGS

An embodiment of the invention will now be described by way of example and with reference to the accompanying drawings in which.

DETAILED DESCRIPTION

Figure 1:
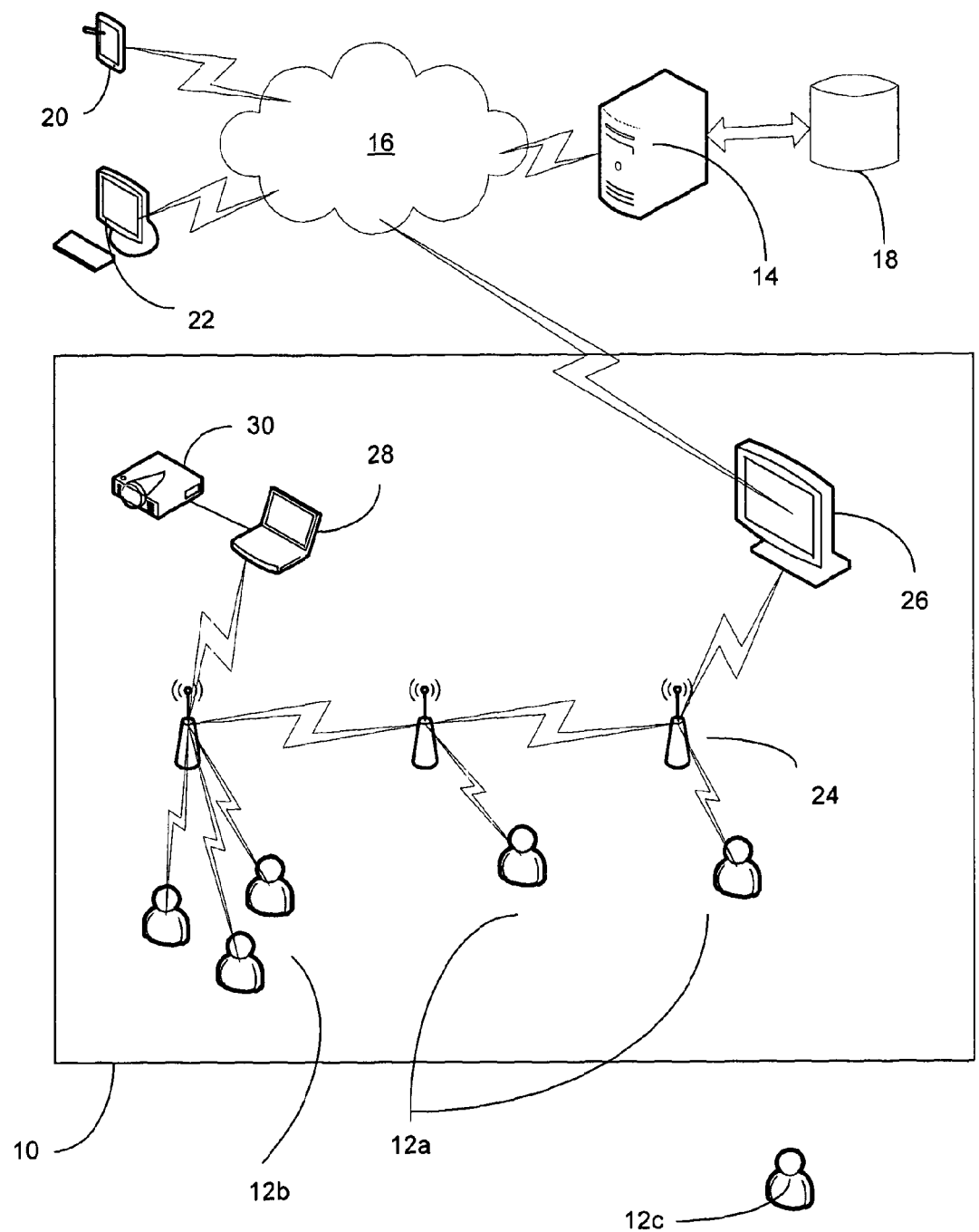
FIG. 1 shows schematically a physical activity monitoring system in accordance with an embodiment of the invention.

FIG. 1 illustrates a physical activity monitoring system deployed, in this example, in a health club 10. The system caters for a plurality of users 12 and is scalable to serve several hundred users in a single health club installation.

Each user 12 has a heart rate monitor belt (discussed in more detail further below with reference to FIG. 3) assigned to them and is registered as a user of the system.

As registered user, an account is maintained for them at a remote data management server 14, in this example a web server that is connected to other components of the system via the Internet 16. The server 14 has an associated data store 18, which may be located physically adjacent the server 14 (e.g. in the same rack or casing) or remote from the server. The data store 18 stores each user's account information, including physical activity data that has been uploaded to their account in the manner discussed below.

Authorised users, including the account holder themselves but potentially also including others (such as health club employees, fitness trainers, medical practitioners, the employer or school of the account holder, etc) are able to access the account data from their own Internet connected devices 20, 22 by connecting to the data management server 14 over the Internet 16. Access to the account data can be controlled in a conventional fashion to restrict access to each account only to those users authorised to view the respective account data.

Typically, the data management server 14 will manage the storage of data and accounts for multiple health clubs (or other system installations), although for convenience only a single health club installation 10 is shown here.

In the health club itself, data is transmitted from each user's 12a, 12b heart rate monitor belt to receiver stations 24. In this example there are three receiver stations that are daisy chained together with wireless links. In other installations more or fewer receiver stations might be used and the links could be hard wired rather than wireless or a combination of hard wired and wireless. The number of receiver stations can be selected to give a desired coverage and to cater for the expected number of users. Typically each receiver station 24 will have a range of at least 50 meters and will be able to have up to 100 users connected simultaneously.

The data received by the receiver stations 24 is sent (again, wirelessly in this example) to a hub 26, referred to in the following as a "kiosk". From the kiosk 26 the data is sent via the Internet 16 to the data management server 14.

The kiosk 26 may itself also serve as a receiver station. If a receiver is incorporated in the kiosk 26 it is preferably shielded to avoid interference from other components of the kiosk. The kiosk preferably has a non-interruptible power supply.

The kiosk in this example comprises a conventional PC (e.g. running a Windows 7 operating system). Preferably it is a touch screen PC. The function of the PC is controlled by bespoke software installed on the PC that controls its operation to received and send on the heart beat data from the user's belts. The kiosk may also do some processing of the data, for example to convert the raw heart beat data into percentage effort data and/or calories burned data that can be displayed to the user at the kiosk. Additionally or alternatively, derived data such as percentage effort and calories burned can be calculated by the data management server 14 and stored in the data store 18, from where it can be retrieved by a user on their own device 20, 22 or at the kiosk 26.

The software executing on the kiosk can also provide a console facility that enables existing users to view and update their account data and that may also allow new users to register and create a new account.

In this example, the health club installation also includes a studio console 28 that receives heart rate data for users 12b participating in a group exercise class. This data, or data derived from it (e.g. percentage effort) can then be output to a display device 30, such as a projector, so the data can be displayed in real time during the class. As with the kiosk, the studio console can comprise a conventional PC executing software to manage the capture and display of the heart rate data. The studio console 28 may have an integral receiver station or may receive data from one of the other receiver stations either directly or via the kiosk 26.

When a user 12c is away from the health club 10, they can still use their heart rate belt to record and store heart rate data, which can then be uploaded to the data management server 14, via the receiver stations 24 and kiosk 26 when the user next visits the health club 10.

Figure 3:
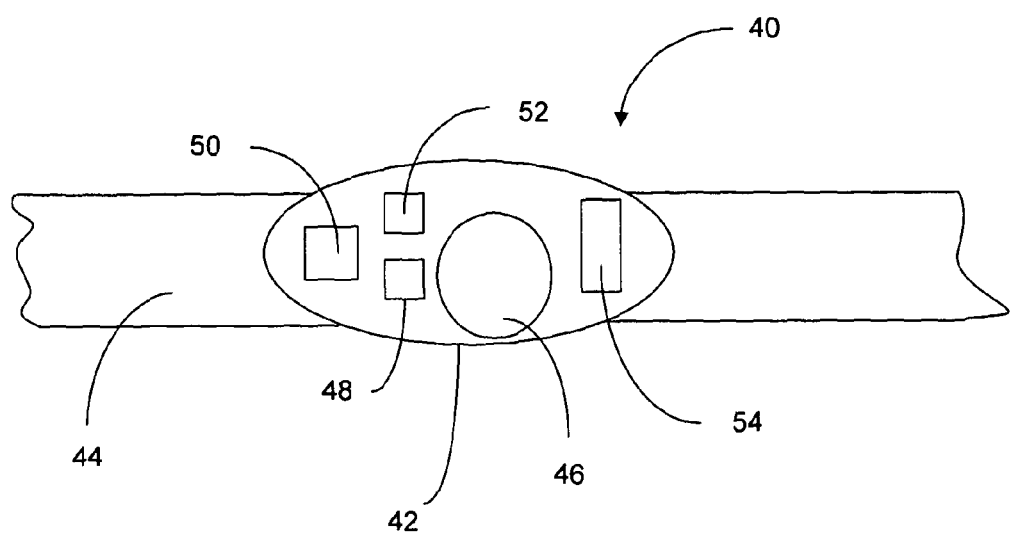
FIG. 3 shows schematically a heart rate monitor that can be used with the system of FIG. 1.

FIG. 3 shows schematically a heart rate monitor belt 40 for use with the system of FIG. 1. The monitor 40 includes an electronics package 42 that is carried by a belt 44 that can be strapped around the user's chest. The package 42 and belt 44 are preferably sweat and water resistant and may be waterproof in some embodiments.

The electronics package includes a detector 46 for detecting EKG signals and producing corresponding heart beat data, a memory 48 for storing the heart beat data and a transmitter 50 for transmitting the heart beat data to the receiving stations 24. The operation of the heart beat monitor is controlled by a processor 52 and is powered by a battery 54, which in this example can be replaced by the user.

The transmitter in this example is an ANT+ transmitter. Other types of transmitter can be used and in some examples the monitor can include multiple transmitters of different types, for example an ANT+ transmitter and a 'Bluetooth LE' transmitter.

The data transmitted from the heart rate monitor 40 to the receiver station 24 includes the heart rate data itself and preferably also includes a unique identifier for the monitor 40 and/or the user 12, so that the data can be associated with the correct user account when it is uploaded. The data also includes timestamp data (date and time) associated with the heart beat data to allow temporal tracking of the heart beat data. This timestamp data is saved with the heart beat data in the memory 48.

In some examples, the transmitter 50 may also be a receiver to allow two-way communication between the heart rate monitor 40 and the receiving stations 24. This can be useful, for example, to enable the receiving station to inform the monitor when data has been successfully uploaded (before it is deleted from the memory in the belt) and or to allow polling of the monitors by the receiving stations or vice versa to determine when they are within range of one another.

Figure 2:
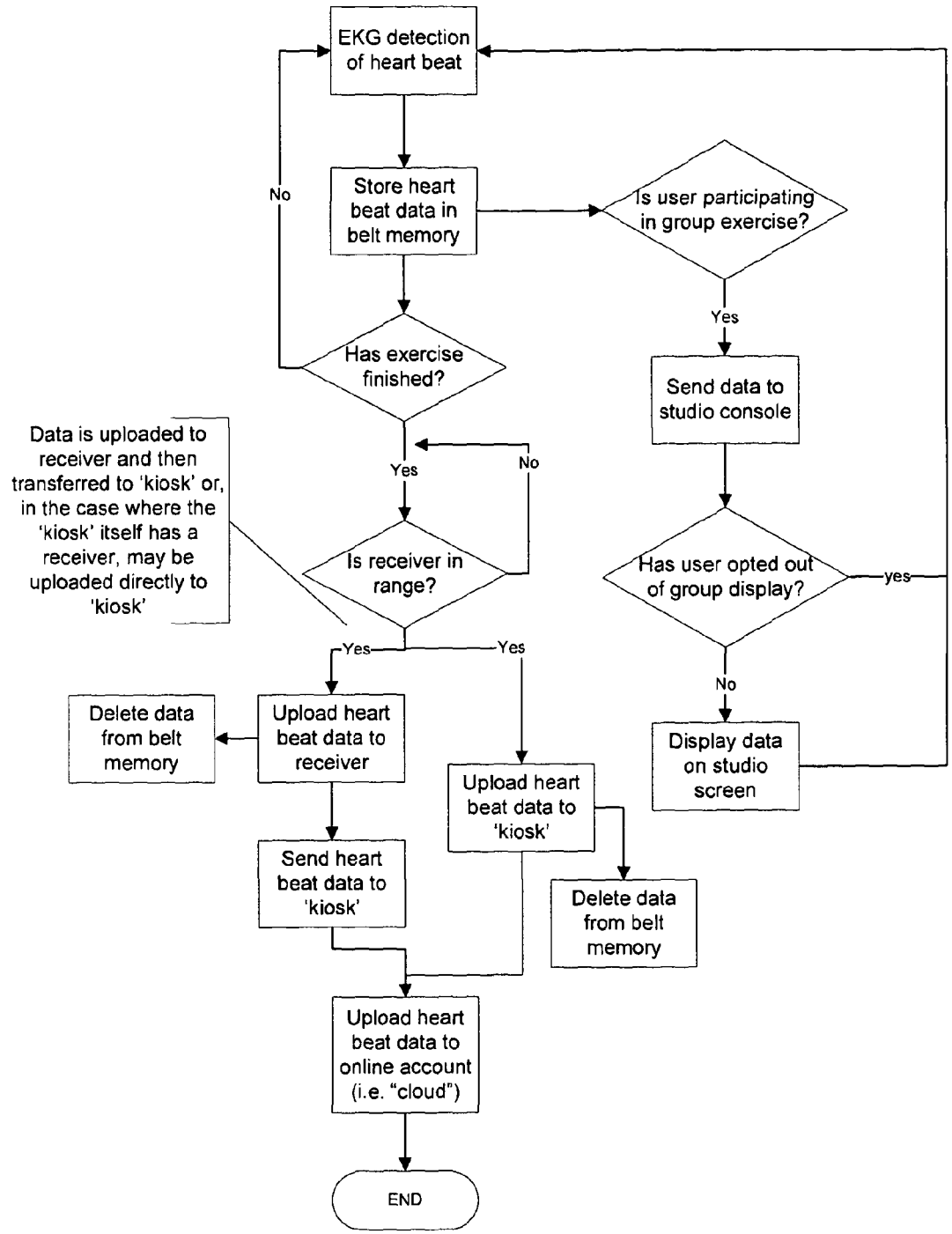
FIG. 2 illustrates the operation of the system of FIG. 1.

Turning to FIG. 2, the operation of the system will now be described.

Initially, once a user starts to exercise, having put on the chest strap monitor 40, the monitor starts to detect and store the heart beat data in the monitor's memory 48. In this example, this detecting and local storing process continues until a break in the exercise, at which point the data is uploaded to a receiver station if one is within range. If no receiver station is within range then the monitor periodically checks to see if it has come within range of a receiver and uploads the data once it is within range. Once the data has been uploaded it is deleted from the monitor memory.

The data that has been uploaded to the receiver station is subsequently transmitted to the kiosk, from where it is uploaded over the Internet to the users online account ("in the cloud") at the data management server. In some cases the kiosk itself will have an integral receiver so the data will be uploaded from the belt directly to the kiosk, from where it will be sent to the cloud.

In the case where the user is participating in a group exercise class, rather than wait until completion of the exercise, the heart rate data is uploaded regularly during the course of the class to the studio console. Unless the user has opted to not have their data displayed, the studio console then operates to display the user's heart rate data to the class along with data for the other class participants, on a single display. The data will typically be presented in the form of a percentage effort (i.e. percentage of HRmax). The user may elect in advance to have their data displayed alongside their actual name, a nick name or anonymously (or not at all).

As will be appreciated from the above example, embodiments of the invention provide a unique solution that allows health clubs to capture accurate activity data within their 4 walls as well as from activity outdoors. It can allow owners/operators a way to further interact with their members whilst at the same time helping them to achieve their health and fitness goals. It allows operators to drive secondary revenues through heart rate belt sales, increased personal/group training revenues and membership options.

Embodiments of the invention can make heart rate training easy to understand, scaleable and relevant to members of the health club. They simply purchase their own heart rate monitor belt (or are given one by the club) which they wear on the health club floor or in studio classes. Their % effort level and real time calories can then be displayed on a screen in the club/class to tell them what intensity they are working at and whether to push harder or ease off. The user can choose to show their name, nickname or even favorite movie star if they prefer to remain anonymous! Or they can opt out of being shown on screen and simply just record their activity data for them to review later.

Once the user has finished their workout their activity data is automatically sent to the kiosk in the club which uploads their activity to their personal online account. Here members can view all of their exercise history and biometric data, set themselves goals and even take part in club challenges with other users. Owners/operators also have access to this user data and are able to set monthly reports to support member retention.

The monitor belt can also be used when away from the club storing activity data within the belts memory function. In order to upload their data users have to return to the club where it is wirelessly uploaded to the kiosk. This encourages members to keep returning to the club in order to view their latest workout, rather than allowing them to do this at home as it means clubs become an integral part of their experience.

The described approach can also allow clubs to connect with their local community. Clubs can link with local offices who want to encourage their employees to be more active by selling monitor belts to them. They can then create a link between their kiosk and the corporate offices' kiosk. Employers may then chose to incentivise their employees to be more active and are able to monitor and track this and health clubs not only benefit from the revenue from belt sales but also a potential new member.

The system can also be offered to local schools, again purchasing belts through a local health club, who then open up whole new market of potential members whilst encouraging children to be more active.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the scope of the invention.

The invention claimed is:

1. A system for monitoring physical activity, the system comprising:
- a plurality of heart rate monitors that can be assigned to individuals, each heart rate monitor comprising a detector for creating heart rate data that provides a measure of the individual's heart rate, a memory for storing the heart rate data, and a transmitter for transmitting the heart rate data;
- at least one receiver station comprising a receiver for receiving heart rate data transmitted from the plurality of heart rate monitors;
- a data management server connected by a communications network to the receiver station, to receive the heart rate data from the receiver station over the network; and
- a database associated with the data management server for storing the heart rate data received by the data management server;
- wherein each heart rate monitor is configured to automatically transfer the heart rate data to the receiver station when the heart rate monitor is in range of the at least one receiver station and to store heart rate data in the memory when the heart rate monitor is not in range of the at least one receiver station, the at least one receiver station being configured to transmit a polling signal for detection by the heart rate monitor or the heart rate monitor being configured to transmit a polling signal for detection by the receiver in order to determine when the heart rate monitor is in range of the receiver station.

2. The system according to claim 1, wherein the heart rate monitors are chest belts.

3. The system according to claim 1, wherein the memory for the heart rate monitor is non-volatile memory is integrated with the heart rate monitor.

4. The system according to claim 1, wherein the transmitter for the heart rate monitor is selected from the group consisting of: an analogue radio transmitter, an ANT+ transmitter, a 'blue tooth' transmitter, and a 'blue tooth LE' transmitter.

5. The system according to claim 1, wherein the heart rate monitor comprises multiple transmitters of different types.

6. The system according to claim 1, wherein the range of the transmitter is at least 50 meters.

7. The system according to claim 1, wherein the heart rate monitor is configured to automatically transfer the heart rate data to the receiver station.

8. The system according to claim 7, wherein the data is transmitted at the end of an exercise session, the end of an exercise session being determined by a pre-determined period of inactivity.

9. The system according to claim 1, wherein the transmitter is integrated with the heart rate monitor.

10. The system according to claim 1, wherein the receiver station is capable of receiving heart beat data from at least 100 heart beat monitors.

11. The system according to claim 1, comprising a plurality of receiver stations installed in a given location, the system further comprising a hub to which each of the receiver stations is connected via a communication link and via which data from each of the receiver stations is sent to the data management server.

12. The system according to claim 11, wherein the hub incorporates a management console for managing aspects of the system.

13. The system according to claim 1, wherein the data management server provides access to the stored heart rate data and/or data derived from the heart rate data.

14. The system according to claim 1, further comprising a studio console that incorporates or is linked to a receiver station, the studio console being configured to receive heart rate data from the plurality of heart rate monitors and to provide a display output that can drive one or more screens to display the heart rate data, or data derived from it, for one or more users.

15. The system according to claim 1, wherein the communications network via which the receiver stations are connected to the data management server is the Internet.

16. The system of claim 1, further comprising a heart rate monitor, the heart rate monitor comprising a detector for creating heart rate data that provides a measure of an individual's heart rate, a memory for storing the heart rate data, and a transmitter for transmitting the heart rate data to a receiver station, wherein the detector, memory and transmitter are incorporated in a single package.

17. The system of claim 1, further comprising a receiver station, the receiver station comprising a receiver for receiving heart rate data transmitted from the plurality of heart rate monitors.

18. The system of claim 1, further comprising a data management server, the data management server being connectable by a communications network to a receiver station, to receive the heart rate data from the receiver station over the network and having an associated database for storing heart rate data received by the data management server.

19. The system of claim 1, further comprising a hub, the hub comprising a communications link that connects a plurality of receiver stations, the hub further comprising an integral receiver station.

20. A method of collecting physical activity data from a plurality of individuals, each individual having been provided with a heart rate monitor capable of recording and storing heart rate data and transmitting the heart rate data to a receiving station, the method comprising:
- transmitting, via the receiving station, a polling signal detectable by the heart rate monitors or detecting, via the receiving station, a polling signal transmitted by a heart rate monitor to determine whether a heart rate monitor is in range of the receiving station;
- receiving at the receiving station, heart rate data for the plurality of individuals from their respective heart rate monitors when the monitors are in range to transmit data to the receiving station; and
- sending received heart rate data from the receiving station to a data management server over a communications network.

21. The method according to claim 20, wherein the step of sending heart rate data to the data management server comprises sending the data from the receiving station to a hub, the hub being shared by a plurality of receiving stations, and sending the data from the hub to the data management server over the communications network.

22. The method according to claim 20, wherein the receiving station is located in a health club.

23. A computer program comprising computer program code that when executed on a computer or a computer network can cause the computer or computer network to function as one or more of:
 the receiver station of the system of claim 1;
 the hub of the system of claim 1; and
 the data management server of the system of claim 1.

24. The computer program comprising computer program code that when executed on a computer or a computer network can cause the computer or computer network to operate in accordance with the method of claim 20.

25. A system according to claim 1, wherein the heart rate data is transmitted continuously from the heart rate monitor to the receiver station when the heart rate monitor is in range of the receiver station.

\* \* \* \* \*